United States Patent [19]

Ross et al.

[11] Patent Number: 4,800,893
[45] Date of Patent: Jan. 31, 1989

[54] KINESTHETIC PHYSICAL MOVEMENT FEEDBACK DISPLAY FOR CONTROLLING THE NERVOUS SYSTEM OF A LIVING ORGANISM

[76] Inventors: Sidney A. Ross; Mark J. Ross, both of 6901 Katherine Ave., Van Nuys, Calif. 91405

[21] Appl. No.: 61,156

[22] Filed: Jun. 10, 1987

[51] Int. Cl.⁴ ............................................. A61B 5/04
[52] U.S. Cl. ..................................... 128/732; 128/905
[58] Field of Search .................................... 128/731–3, 128/905; 340/724–727

[56] References Cited

U.S. PATENT DOCUMENTS

| | | | |
|---|---|---|---|
| 3,837,331 | 9/1974 | Ross | 128/1 C |
| 3,855,998 | 12/1974 | Hidalgo-Briceno | 128/732 |
| 3,893,450 | 7/1975 | Ertl | 128/731 |
| 3,967,616 | 7/1976 | Ross | 128/732 X |
| 3,978,847 | 9/1976 | Fehmi et al. | 128/732 |
| 4,140,997 | 2/1979 | Brady | 128/732 |
| 4,354,505 | 10/1982 | Shiga | 128/732 |
| 4,632,126 | 12/1986 | Aguilar | 128/732 |
| 4,690,142 | 9/1987 | Ross et al. | 128/419 R |

FOREIGN PATENT DOCUMENTS 8700746 12/1987 PCT Int'l Appl. ................. 128/731

*Primary Examiner*—Max Hindenburg
*Assistant Examiner*—Angela D. Sykes
*Attorney, Agent, or Firm*—Blakely, Sokoloff, Taylor & Zafman

[57] ABSTRACT

A method and system for providing as a biofeedback signal a visual display showing kinesthetic physical movement to enable a subject to produce desired thought patterns. Sensors or electrodes are connected to the subject at one or more topological locations. The signals detected by the sensors are input to a conventional EEG device. The EEG output is processed into one or more analog voltage signals. These analog signals are input to a computer which generates a video display and audio if desired. The image on the display depicts kinesthetic physical movement as a function of the analog voltage.

56 Claims, 4 Drawing Sheets

KINESTHETIC PHYSICAL MOVEMENT FEEDBACK DISPLAY FOR CONTROLLING THE NERVOUS SYSTEM OF A LIVING ORGANISM

BACKGROUND OF THE INVENTION

1. Field of the Invention

This invention relates in general to the field which has become known as the biofeedback field, and more particularly to a system which utilizes the conscious and subconscious physiological interactions between the visual stimulus and the neuronal pathways of the nervous system of a living organism, and a method for training the organism to control the waveform patterns of its bioelectrical signals for therapeutic or other purposes.

2. Prior Art

Disorders of the nervous system, such as epilepsy, have traditionally been treated by pharmaceutical and/or surgical procedures. My earlier inventions disclosed in U.S. Pat. Nos. 3,837,331 and 3,967,616 describe an alternative method for treating these disorders. The present invention is based upon the discovery that a living organism, typically an animal high on the intelligence scale, can control its brainwave patterns and bring about permanent or long-lasting changes thereto by a process of learning and, further, that the changes induced in the bioelectrical patterns can be such as to result in the substantial control of epileptic seizures, hyperkinesis, insomnia, depression and head trauma. Thus the present invention provides a safe and practical method and system enabling the application of this discovery in many fields including neurological therapy and brain research.

In the prior art, biofeedback training has been conducted using visual, audio and tactile feedback (current U.S. patent application Ser. No. 215,027 now U.S. Pat. No. 4,690,142). These feedback modalities as used in the past either alone or in combination with one another provided a certain degree of effectiveness depending upon the type of treatment and the individual patient. Visual feedback often was accomplished with lamps, meters and video displays. Lamp displays and meter displays often lost the interest of the patient in a short period of time. Video displays often only imitated the lamp and meter displays with colored bar graphs. A few added squiggly lines which followed an input waveform, and fewer added some type of simple animated graphics. With some therapies the treatment was effective but took long periods of time to accomplish the desired goals. Heretofore, the prior art has not disclosed a means or a method of presenting a visual display that is specifically designed to facilitate brainwave training as effectively as the present invented method and system. The present invention is based on the discovery that visual images of kinesthetic physical movement, when displayed as feedback for particular neurological signals, can improve the therapeutic biofeedback training of certain neurological disorders, thereby achieving new and beneficial results. In view of this discovery, the present invention teaches a means and a method by which such therapeutic biofeedback training can be carried out.

BRIEF SUMMARY OF THE INVENTION

The present invention takes biofeedback one step further than the previous state of the art which allowed the patient to modify some physiological characteristic of interest by following cues presented to him or her by the biofeedback instrument. The present invention introduces a means and a method to help the patient to elicit the proper type of thought patterns which facilitate the proper training to modify certain physiological characteristics. This invention is primarily designed for the treatment of neurological disorders such as epileptic seizures, hyperkinesis, insomnia, depression and head trauma but is not limited to the aforementioned disorders or to neurological disorders.

The present invention normally utilizes, but is not limited to, EEG electrode placement over the sensory motor cortex. The most often used bipolar lead locations are C3 and C5. Another common bipolar lead pair location are C2 and C4 which may be used when a seizure focus is found on the right hemisphere of the brain. These letter and number combinations refer to international lead symbols. The electrode pairs are normally referenced to a ground or reference electrode which is often an earclip electrode.

The sensory motor rhythm also called SMR is a brainwave pattern found over the central motor cortex. The SMR is instrumental in treating the neurological disorders mentioned above. This brainwave pattern is often difficult to detect in some patients, particularly in most but not all seizure patients. It is often a tiny subdominant signal lost in the presence of much larger dominant signals.

The normal SMR biofeedback training consists of typing to increase the amplitude and duration of the patient's SMR while simultaneously trying to inhibit the undesired high amplitude signals. This is normally conducted with the utilization of numerous channels of filters and amplitude detecting means, as well as logic and timing circuitry and a complex feedback display system.

Production of the SMR in a patient is often accomplished while the patient is sitting in a relaxed posture, alert and concentrating on a physical activity while physically inactive and receiving feedback from the invented system.

Many quadriplegics produce very large SMR signals in their EEG without trying; it is just there. This is assumed to be brought about by the fact that they no longer have control over the movement of their arms and legs. There is a certain parallel between the naturally produced high amplitude SMR in the quadriplegic and the ability of patients undergoing SMR biofeedback training to learn to produce larger amounts of SMR while in a physically relaxed state and thinking of physical activity while receiving feedback from the invented system.

The invented system presents as part of its feedback to the patient a visual display showing kinesthetic physical movement which is designed to help elicit the proper thought patterns to help improve the patient's biofeedback training. The main focus of interest on the display is a man who through visual animation techniques is normally depicted as running. His motion includes arms and legs moving. The man runs up and down three downward moving escalators. His position higher or lower on the escalators is determined by the amount of SMR the patient is producing; the more SMR produced at an time the higher the man is on the escalators. The important point of the invention is not just a man running up and down the escalators but the fact that the image is tied to the production of a particular brainwave pattern; the image is designed to elicit the proper thought patterns to help produce the desired brainwave pattern.

When the patient produces undesired brainwave patterns, the visual display changes to indicate this condition; the man on the screen is shown down on the floor on his knees banging the floor with his fists.

The animation of the screen is accompanied with audio output which indicates all the motion on the screen. Numerous scores are totalled on the screen to indicate the level of progress and how much time was spent with undesired brainwave patterns taking over the control of the screen.

The circuitry used in the invention utilizes readily available EEG amplifiers, filters, integrators, amplitude detectors, timing circuits, logic circuits, a small computer for generating the visual and audio display, and a video display.

The invented method requires the subject human organism utilizing its cognitive powers to alter the particular characteristics of its detected bioelectrical signals, which are detected by conventional EEG means, so as to cause the visual display to change in a preconceived manner, e.g., to cause the man in the display to run up the escalators. The preconceived condition of the visual display is, of course, related to certain desired waveform patterns of the original detected bioelectrical signals, or more specifically, to the attainment of one or more desired characteristics in those signals.

By repeatedly exercising a subject in the manner just described, i.e., by extensive training utilizing the present invention, the subject can learn to control its brainwave patterns for therapeutic or other purposes.

The particular treatment to be performed dictates from where the bioelectrical signals will be detected, what characteristics will be desired, and what characteristics will be undesired. The exact image on the visual display is also a function of the particular treatment. For this reason it should be understood that the invented system is not a fixed single structure but rather a combination of means whose specific embodiments are adapted to suit particular applications. Similarly, the invented system is typically tuned and calibrated in accordance with the requirements of each application to which it is to be applied. This invention also contemplates a combination of means sufficient to enable multipurpose use in a number of applications either simultaneously or by sequential selection.

Thus, it is a principal object of this invention to provide a practical and safe method and system to enable a living organism to control significant characteristics o its nervous system.

Other objects, novel features and advantages of the present invention will become apparent upon making reference to the following detailed description and the accompanying drawings. The description and the drawings will also further disclose the characteristics of this invention, both as to its structure and its mode of operation. Although a preferred embodiment of the invention is described hereinbelow, and shown in the accompanying drawings, it is expressly understood that the description and drawings thereof are for the purpose of illustration only and do not limit the scope of this invention.

DETAILED DESCRIPTION OF THE INVENTION

With reference to FIGS. 1, 2, 3 and 4, the invented system is now described in detail. Like elements in each figure will be designated by like numerical designations. The invented method will be described in conjunction with the description o the operation of the system. For the purposes of this description the living organism will be a human being and the nervous system involved will be the brain. It should be understood, however, that the invention is not so limited.

Figure 1:
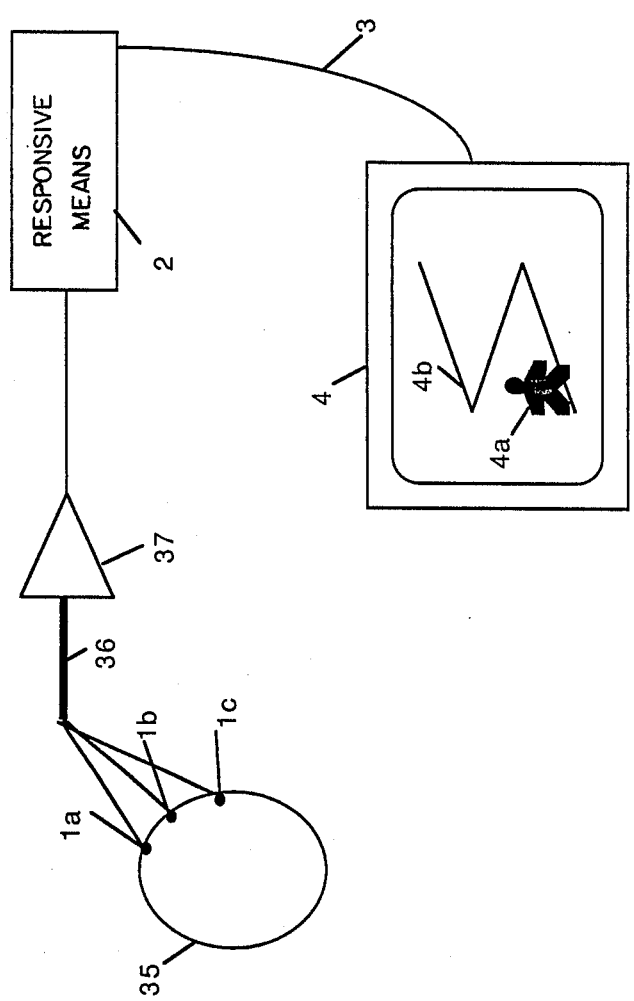
FIG. 1 is a block diagram of one embodiment of the invented system.

In FIG. 1, a human subject is shown with his skull 35 connected to electrodes 1a, 1b and 1c, electrode cable 36 and an EEG amplifier 37. Electrodes 1a, 1b and 1c are affixed to the skull 35 of the human subject and detect the bioelectrical signals generated in the topological regions of the brain at which they are affixed. Such signals are commonly referred to as EEG signals. The EEG signals detected by the electrodes 1a, 1b and 1c are sent to the EEG amplifier 37 by means of the electrode cable 36. EEG amplifiers are typically high gain very low noise amplifiers which have high common mode rejection ratios and are often found in EEG and polygraph recorders. These amplifiers often contain line frequency rejection filters. The amplified EEG signal coming out of amplifier 37 is routed to responsive means 2 for signal processing. A typical responsive means is described in conjunction with FIG. 4. The output of the responsive means shown in FIG. 1 is called the first output signal 3. This first output signal 3 is sent to the visual display 4 which presents a visual image of a man 4a running up and down three downward moving escalators to the human subject First output signal 3 is typically an analog signal representing an amount as a voltage level.

Visual display 4 comprises standard off-the-shelf devices for converting an electrical signal into a visual presentation. These devices typically include a computer interfaced to the input signal and a suitable display device such as a computer monitor or television set. The computer typically is programmed with software which acts with the computer hardware to generate the proper signals necessary to produce the desired visual images and, when desired, audio output from the display device. Visual display 4 is programmed to produce an image depicting kinesthetic physical movement. The operation and general content of such software is set forth in this description; however, a specific listing of such software for a Radio Shack Color Computer is appended to this specification. Other means commonly exist for generating the visual display, such as video techniques including disks, holography and other more complex computer methods, and as such my invention is not limited to the above description.

The human subject observes the visual display 4 which is controlled by his own detected and amplified EEG signals processed by the responsive means 2. The image depicting kinesthetic physical movement observed on the visual display 4 is designed to elicit thoughts of physical motion and exertion. This image simultaneously indicates the amount of compliance the subject is reaching with regard to predetermined desire and/or undesired conditions. The displayed image has an inherent relationship with the EEG signals detected at specific topological locations. Typically the human subject is sitting in a relaxed posture while thinking thoughts of physical motion and exertion.

Figure 2:
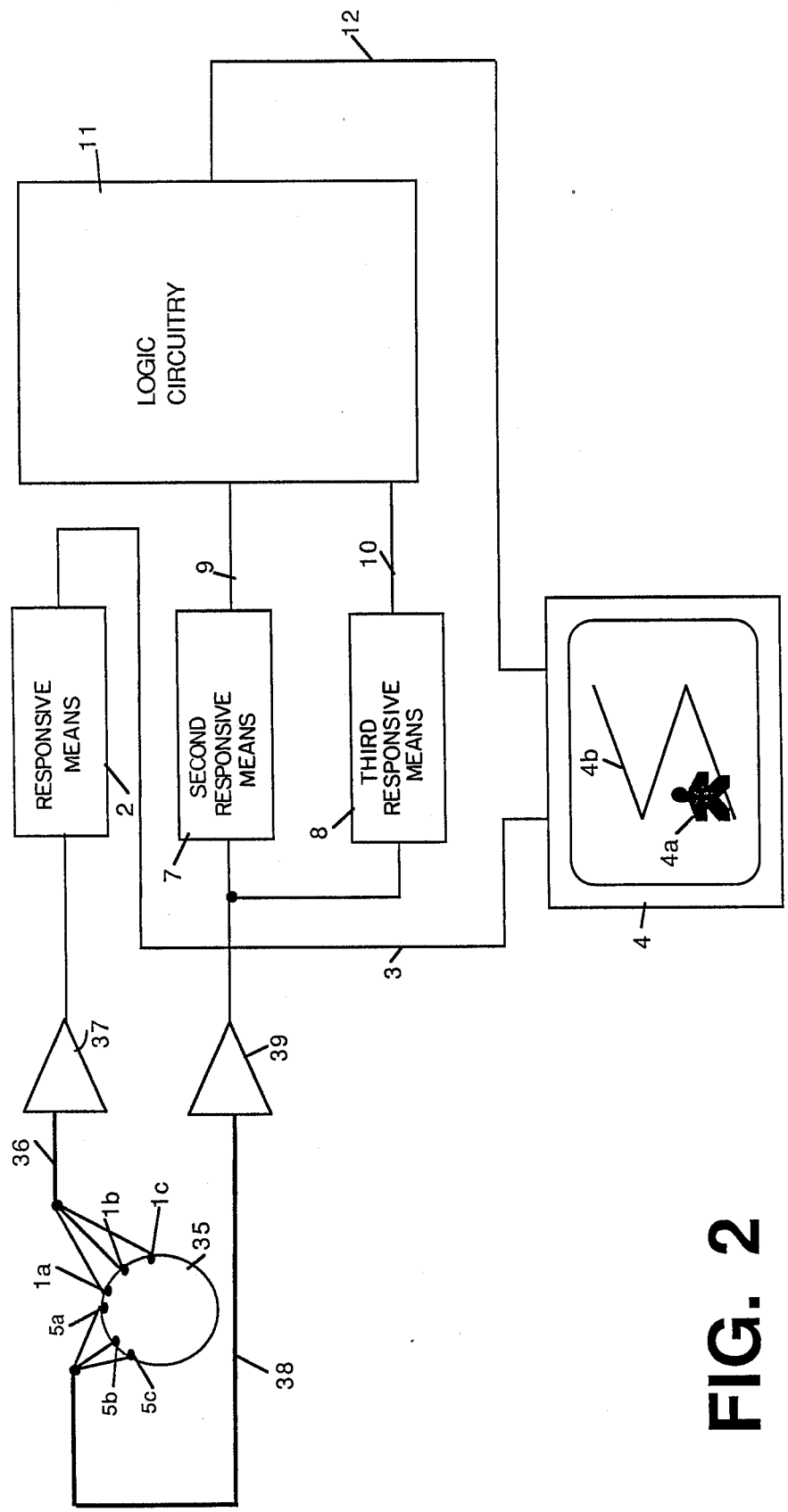
FIG. 2 is a block diagram of the elements comprising two detecting means driving multiple responsive means combined into one logic means.

FIG. 2 depicts an embodiment of the present invention whereby EEG signals detected from two different topological area of the skull 35 may be processed and incorporated into one visual display. Also depicted are multiple responsive means 2, 7 and 8 and logic means 11.

A first EEG detecting means comprised of electrodes 1a, 1b and 1c, electrode cable 36 and EEG amplifier 37 detect EEG signals from one topological area of the human subject's skull 35 and direct the detected and amplified EEG signal to responsive means 2 as demonstrated in FIG. 1. The first output signal 3 from responsive means 2 drives visual display 4.

The second EEG detecting means comprised of electrodes 5a, 5b and 5c, electrode cable 38 and EEG amplifier 39 is depicted detecting EEG signals from a different topological area of the human subject's skull 35. The output from EEG amplifier 39 is directed to two responsive means 7 and 8 for signal processing. Responsive means 7 sends its output 9 to first input of logic means 11, and responsive means 8 sends its output 10 to a second input of logic means 11.

Input signals 9 and 10 are processed in logic means 11 and a resultant second output signal 12 is fed to the analog display 4. Typical responsive means and logic means 11 are described in conjunction with FIG. 4.

An example of the operation of the embodiment shown in FIG. 2 follows. The first EEG detecting means is configured so as to detect a signal which may contain desirable bioelectrical components. Responsive means 2 processes this signal and produces a first output signal 3 whose amplitude is directly proportional to the amount of the desirable bioelectrical components detected in the EEG signal This amplitude modulated first output signal 3 is sent to the visual display 4. The visual display 4 will respond to the amplitude of the first output signal by producing an image which varies with the first output signal. The second EEG detecting means is configured so as to detect signals which may contain undesirable bioelectrical components. Responsive means 7 and 8 process these signals and, when undesirable signals are detected, produce an output signal 9 or 10 respectively or both 9 and 10 if both responsive means 7 and 8 produce signals simultaneously. When either input to the logic means 11 contains an on signal, a signal is transmitted on the second output signal 12 line to the visual display 4 which modifies the image on the display produced by the first output signal 3. This allows the human subject to know when he is producing desirable bioelectrical components, to know how much of the desirable bioelectrical components he is producing, and to know when he is producing undesirable bioelectrical components.

Figure 3:
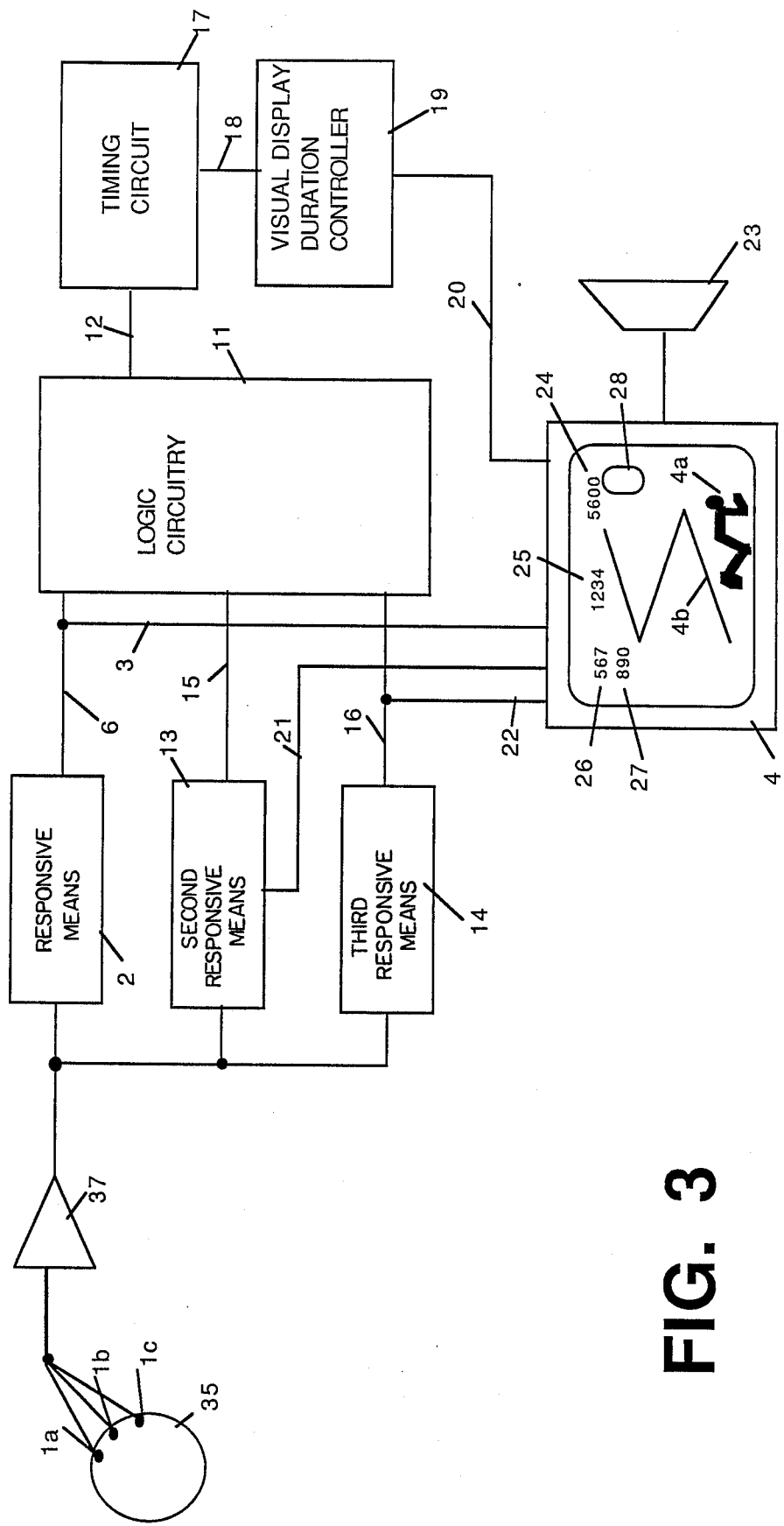
FIG. 3 is a lock diagram of the elements comprising one detecting means driving multiple responsive means.

FIG. 3 shows an embodiment of the present invention whereby EEG signals which are detected from one topological area of the skull are processed in multiple responsive means, logically recombined, and timed for more precise control of the visual display 4, and additionally includes audio output as an adjunct to the feedback as well as a total information display of quantified performance.

The skull 35 of the subject is connected to electrodes 1a, 1b and 1c, electrode cable 36 and an EEG amplifier 37 as described in FIG. 1. The amplified EEG signal is sent to three responsive means 2, 13 and 14 for processing. Responsive means 2 is depicted as detecting a desired bioelectrical signal. The first output signal 3 from responsive means 2 acts as an analog control of the image on the visual display 4 as in the embodiment of FIG. 2. An additional path 6 for the first output signal is sent to the logic means 11.

Responsive means 13 and 14 are both depicted as detecting undesired bioelectrical signals. When responsive means 13 detects an undesired bioelectrical signal, it sends an output signal 15 to the logic means 11 and a third output signal 21 to the visual display 4. Similarly, when responsive means 14 detects an undesired bioelectrical signal, it sends an output signal 16 to the logic means 11 and a third output signal 22 to the visual display. In the case of responsive means 14 the third output signal 22 is derived from the first output signal 16. Responsive means 2, 13 and 14 as well as logic means 11 are described in conjunction with FIG. 4.

Logic means 11 combines the outputs of the three responsive means. If a proper signal from responsive means 2 is received and no undesired signal from either responsive means 13 or 14 is received, then logic means 11 sends out a second output signal 12 to timing circuit 17. Timing circuit 17 typically requires a continuous input signal of 500 milliseconds to activate its output signal 18 called the timed second output signal. This timed second output signal 18 activates the visual display duration controller 19 which controls exactly how long a signal will be given to the visual display 4 through output 20. This timing ma be critical in order for the visual display 4 to sample its input line 20 to distinguish between two adjacent input pulses.

The visual display 4 gives a pictorial image of how much desired bioelectrical signal is produced at any given instant, when a discrete reward is produced, and when an undesired bioelectrical signal is present. The discrete reward is determined by the duration controlled second output signal 20. The amount of desired bioelectrical signal is determined by the amplitude of the first output signal 3. The undesirable bioelectrical signal is determined by the output signals 21 and 22.

As previously described, a typical presentation on the visual display 4 would include a man 4a running up and down three downward moving escalators 4b. His position on the escalators and the direction he is moving is determined by the voltage level of the first output signal 3. As the voltage increases he runs higher up the escalators, and conversely as the voltage decreases he runs down the escalators. At any instant he may not be at the exact position on the escalators corresponding to the input voltage level, but he is trying to approach that exact level. If he were to move as fast as the input voltage changed, the movement would appear too jerky; i.e., brainwave signals can have large and fast fluctuations. The subject tries mentally to make the man on the visual display move as high up the escalators as possible. As the man moves up and down the downward moving escalators his appearance is that of a man running; his arms and legs move with vigor in a fashion that displays kinesthetic physical movement. An audio tone is continuously heard from the audio output transducer 23 which varies in pitch with the voltage level of the first output signal 3; the lower the voltage the lower the frequency and the higher the voltage the higher the frequency. A count is added to the quantified first output signal digital counter 25 according to the input voltage level of the first input signal 3. The higher the voltage level the higher the amount added to this counter. This counter is updated approximately two times a second. It is in effect integrating the voltage level of the first output signal.

When the duration controlled second output signal 20 is present, the man jumps up into the air momentarily, a short melody is heard from the audio output transducer 23, a small reward moves horizontally across the screen from the upper right side of the screen towards the left until it is over the reward barrel 28 at which time the small reward falls into the barrel and 100 points are added to the totalized second output signal digital counter 24.

When an undesirable bioelectrical signal is detected, an input is present on either or both of the output signal lines 21 and/or 22. This causes the man 4a to immediately appear at the bottom of the escalators down on his hands and knees pounding the ground with his hands as shown in FIG. 3. A distinct tone sequence is sounded while the man is in this posture. He remains there until no input is present on either line 21 or 22. As soon as no input is present on either line 21 or 22, the man stands up and starts running up the escalators as before. The signal is not removed from lines 21 and/or 22 the instant the undesirable bioelectrical signal is no longer detected. An intentional delay is added to the removal of the signal on lines 21 and 22. This is to compensate for any artifact which may have been detected by responsive means 2 and allows time for the effect of that artifact to dissipate. Totalized individual third output signal counters 26 and 27 continually accumulate the amount of time lines 21 and 22 respectively are turned on. They present individual totals of the amount of time each undesired bioelectrical signal was detected plus the delay time of the removal of the third output signal. The two lines, 21 and 22, can be fed into one counter if desired instead of two.

Figure 4:
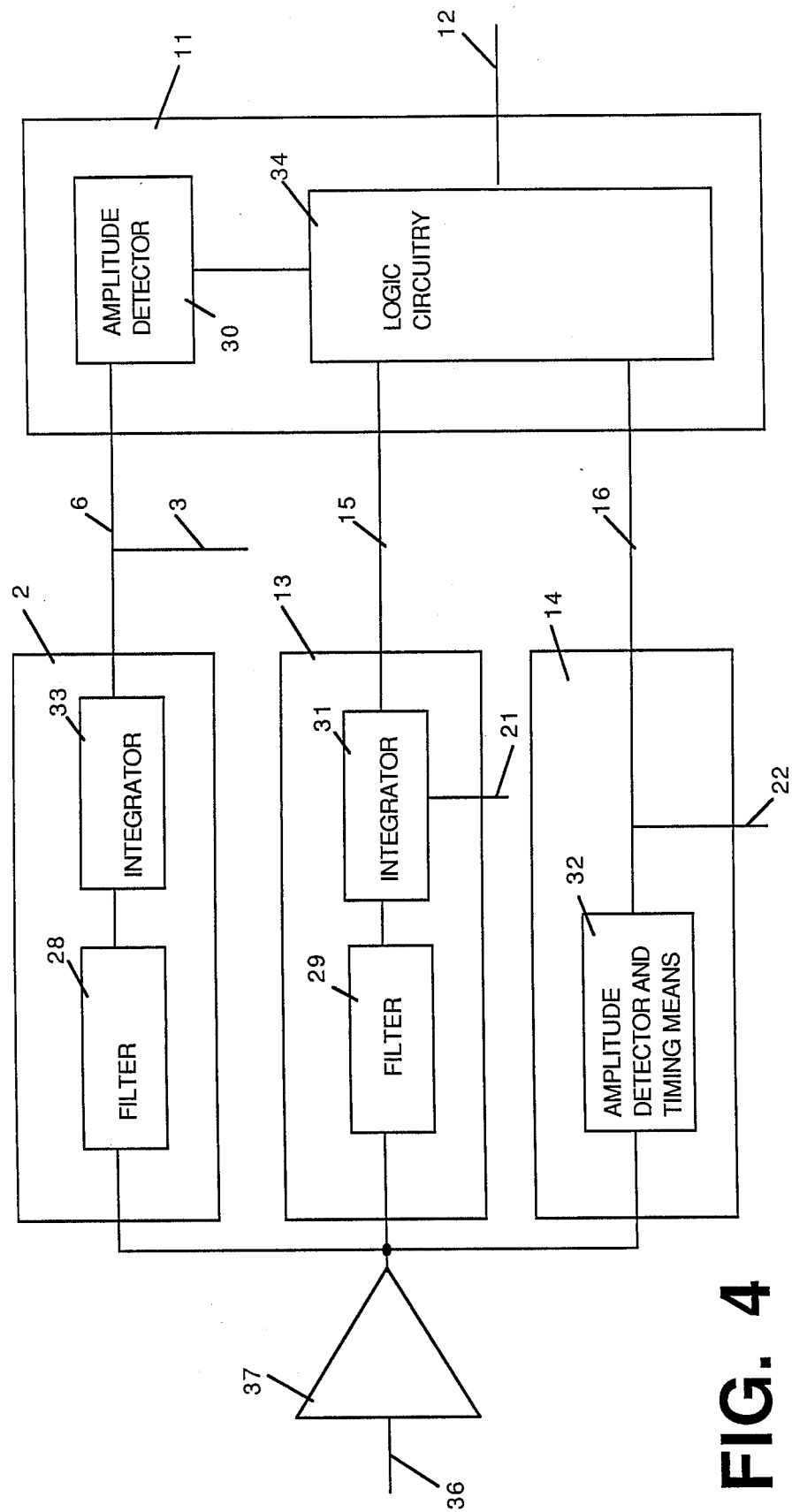
FIG. 4 is a functional block diagram of the multiple responsive means and the logic means of FIG. 3.

FIG. 4 shows the internal components of the responsive means and logic means of FIG. 3 and the responsive means of FIG. 1. Responsive means 2 is used for detecting the desirable bioelectrical signal. The input signal is sent to responsive means 2 from EEG amplifier 37. This signal is sent into filter 28 which is a bandpass filter tuned to the frequency of the desirable bioelectrical signal. The output of filter 28 is sent into integrator 33 which performs a leaky integration on the incoming signal. The leaky integrator has a charge and discharge time constant and acts as an envelope detector with only a small amount of ripple. The output of integrator 33 is an analog signal and is sent to visual display 4 via line 3 and to logic means 11 via line 6. This analog signal controls the position of the man on the escalators on visual display 4. Output signal 6 goes to amplitude detector 30 in logic means 11. Amplitude detector 30 is a voltage detector which turns on when the input voltage exceeds a preset minimum voltage level. Logic circuitry 34 allows the output signal of amplitude detector 34 to be fed onto line 12 if no undesirable signals are detected by either responsive means 13 or 14. The function of line 12 is described by FIG. 3.

Responsive means 13 is used to detect an undesirable bioelectrical signal which falls into a preselected frequency range and is above a preselected minimum amplitude. The input signal is received from amplifier 37 and is fed into filter 29 which is a bandpass filter. The output of filter 29 is sent into amplitude detector and timing means 32. The amplitude detector is a voltage comparator which detects if the output of filter 29 exceeds a preselected minimum voltage level. It detects signals of either polarity, positive or negative. The timing means is used to extend the output period of the amplitude detector for reasons mentioned previously. Output line 21 is sent to visual display 4, and output line 15 is sent to logic circuitry 34 in logic means 11. When an undesirable signal is detected by responsive means 13, line 12 is inhibited by logic circuitry 34 from carrying an output signal.

Responsive means 14 detects any undesired bioelectrical signal above a preselected voltage amplitude. The input signal is received from amplifier 37 and is fed directly into amplitude detector and timing means 32. The amplitude detector is a voltage comparator which detects if the input signal exceeds a preselected minimum voltage level. It detects signals of either polarity, positive or negative. The timing means is used to extend the output period of the amplitude detector for reasons mentioned previously. Output 22 is sent to visual display 4, and output 16 is sent to logic circuitry 34 in logic means 11. When an undesirable signal is detected by responsive means 14, line 12 is inhibited by logic circuitry 34 from carrying an output signal.

Additional responsive means such as responsive means 13 may be added to inhibit the presence of other frequencies. Only one is shown here so as not to clutter up the figures with repetitious circuitry.

We claim:

1. An improved method of controlling the nervous system of a living organism comprising the steps of:
   (a) detecting at least one bioelectrical signal from one or more topological locations in said organism's nervous system;
   (b) passing said at least one bioelectrical signal through at least one electronic means responsive to the presence of at least one characteristic of interest in the waveform of each detected bioelectric signal, each of said responsive means being adapted to provide a first output signal relating to the amount of said characteristic present;
   (c) producing a visual display responsive to said first one or more output signals, said visual display presenting an image depicting kinesthetic physical movement; and
   (d) causing said organism to concentrate mentally so as to change the image depicting kinesthetic physical movement on said visual display, said change of depicted image indicating desired and undesired conditions;
   whereby said organism is trained to alter the waveform pattern of said one or more bioelectrical signals, thereby achieving a desired condition of said nervous system.

2. The method of claim 1 wherein each of said steps is repeated to train the organism to alter the brainwave pattern of said at least one bioelectrical signal to produce a substantially permanent change in said nervous system.

3. The method of claim 2 wherein the audio output is generated when said first output signal, said second output signal and said at least one third output signal are distinct and different from one another.

4. The method of claim 1 wherein said image depicting kinesthetic physical movement is presented to said living organism and is so designed as to elicit thought patterns in said living organism's nervous system which subconsciously affect said nervous system in a manner to cause desired changes in said nervous system, said image so designed facilitating the generation of said thought patterns.

5. The method of claim 1 wherein said image depicting kinesthetic physical movement has an inherent relationship with bioelectrical signals detected at specific topological locations in said organism's nervous system.

6. The method of claim 1 wherein the living organism is alert and in a relaxed posture during the training while observing the image depicting kinesthetic physical movement, thereby concentrating on physical exertion while inhibiting undue physical motion.

7. The method of claim 1 wherein the image depicting kinesthetic physical movement promotes desired thought patterns and displays the degree of compliance in producing said desired and undesired conditions.

8. The method of claim 1 wherein said electrical characteristic of interest in any of said bioelectrical signals is at least one of:
a preselected frequency component thereof;
an amplitude thereof;
a preselected frequency component thereof having an amplitude;
an amplitude thereof greater than a preselected minimum;
a preselected frequency component thereof having a preselected minimum amplitude;
an amplitude thereof less than a preselected maximum;
a preselected frequency component thereof having a preselected maximum amplitude.

9. The method of claim 1 wherein one bioelectrical signal is detected from one topological location in said organism's nervous system and passed through a plurality of said responsive means.

10. The method of claim 1 wherein a plurality of bioelectrical signals is detected from a plurality of topological locations in said organism's nervous system and passed through a plurality of said responsive means.

11. The method of claim 1 wherein a plurality of bioelectrical signals is detected from a plurality of topological locations in said organism's nervous system, and wherein at least one of said bioelectrical signals is passed through at least two of said responsive means, and said other bioelectrical signals, if any, are each passed through at least one additional of said responsive means.

12. The method of claim 1 further comprising the step of determining when said at least one of a first output signal and a plurality of first output signals is present in a predetermined manner indicative of a desired condition of said organism's nervous system, and providing a second output signal when said desired condition is indicated, said second output signal producing a modified image on said visual display.

13. The method of claim 12 including the additional step of passing said second output signal through a timing circuit adapted to detect whether said second output signal is present for a preselected minimum duration and producing said modified visual image only if said second output signal persists for said minimum duration.

14. The method of claim 12 further comprising the step of determining whether at least two of said plurality of first output signals are present.

15. The method of claim 12 wherein said determining step determines whether at least two of said plurality of first output signals are present or absent sequentially in time.

16. The method of claim 12 including, before step (d) of claim 1, the additional steps of:
detecting the presence of at least one undesirable electrical characteristic in the waveform of at least one of said bioelectrical signals;
producing a third output signal when the presence of said at least one undesirable electrical characteristic is detected;
producing multiple distinct third output signals when it is desired to discriminate between two or more of said undesirable electrical characteristics;
modifying the appearance of said visual display if said one or more third output signals are produced;
whereby said organism is informed that at least one undesirable electrical characteristic has been detected.

17. The method of step 16 wherein said undesirable electrical characteristic in said bioelectrical signal is at least one of:
a preselected frequency component thereof;
an amplitude thereof greater than a preselected magnitude; and
a preselected frequency component thereof having a preselected minimum amplitude.

18. The method of claim 16 including the additional step of maintaining the modified appearance of said visual display for a preselected duration once at least one of said undesirable electrical characteristics is detected.

19. The method of claim 16 including the additional step of adding audio output with the visual display when at least one of said third output signals is present.

20. The method of claim 16 including the additional step of totalizing the amount of time said third output signals are present and presenting the updated total in numerical form on the visual display.

21. The method of claim 16 including the additional step of individually totalizing the amount of time each of said multiple distinct third output signals are present and presenting the updated individual totals in numerical form on the visual display.

22. The method of claim 12 including the additional step of adding audio output with the visual display when said second output signal is present.

23. The method of claim 12 including the additional step of totalizing the number of times said second output signal is produced and presenting the updated total in a numerical form on the visual display.

24. The method of claim 1 including, following step (c) thereof, the additional step of controlling the duration of the presentation of said visual display or portions thereof.

25. The method of claim 1 including, following step (c) thereof, the additional step of adding audio output with the visual display responsive to said first one or more output signals.

26. The method of claim 25 wherein said audio output is modulated by the analog of at least one of said output signals.

27. The method of claim 1 including, following step (c) thereof, the additional steps of:
quantifying the amplitude of the first output signal;
totalizing the quantified amplitude of the first output signal over time;

presenting the updated, totalized and quantified amplitude of the first output signal in numerical form on said visual display;

whereby said organism can visualize the amount of the characteristics of interest being produced.

28. An improved method of controlling the nervous system of a living organism comprising the steps of:
(a) detecting at least one bioelectrical signal from at least one topological location in said organism's nervous system;
(b) determining the presence of at least one characteristic of interest in the waveform of each detected bioelectric signal and producing a first output signal relating to the amount of said electrical characteristic present, wherein said electrical characteristic of interest in any of said bioelectrical signals is at least one of:
a preselected frequency component thereof;
an amplitude thereof greater than a preselected minimum; and
a preselected frequency component thereof having a preselected minimum amplitude;
(c) producing a visual display responsive to said first one or more output signals, said visual display presenting an image depicting kinesthetic physical movement;
(d) determining when at least one of a plurality of first output signals is present in a predetermined manner for a predetermined time period indicative of a desired condition of said organism's nervous system, and producing a second output signal when said desired condition is indicated, said second output signal producing a modified image on said visual display;
(e) detecting the presence of at least one undesirable electrical characteristic in the waveform of at least one of said bioelectrical signals, said detected undesirable electrical characteristic producing at least one distinct third output signal, whereby the appearance of said visual display is modified if said at least one distinct third output signal is produced;
(f) maintaining the modified appearance of said visual display for a preselected duration if said at least one distinct third output signal is produced;
(g) adding audio output to the visual display responsive to said first one or more output signals, said audio output modulated by the analog of said one or more output signals;
(h) adding audio output to the visual display when said second output signal is present;
(i) adding audio output to the visual display when at least one of said distinct third output signals is present;
(j) presenting an updated, totalized and quantified amplitude of the first output signal in numerical form on said visual display;
(k) totalizing the number of times said second output signal is produced and presenting the updated total in a numerical form on said visual display;
(l) totalizing the amount of time said at least one distinct third output signal is present and presenting the updated totals in numerical form on said visual display;
(m) causing said organism to concentrate mentally so as to change the image depicting kinesthetic physical movement on said visual display, said change of depicted image indicating desired and undesired conditions;

whereby said organism is trained to alter the waveform pattern of said one or more bioelectrical signals, thereby achieving a desired condition of said nervous system.

29. An improved system of controlling the nervous system of a living organism comprising:
(a) means for detecting a bioelectrical signal disposed at least one topological location on the nervous system of said organism;
(b) electronic means responsive to the presence of at least one electrical characteristic of interest in the waveform of the detected bioelectrical signal, each of said responsive means being electrically couple one of said bioelectrical signal detection means and providing at its output a first output signal relating to the amount of said characteristic of interest;
(c) means for producing a visual display responsive to each of said first output signals, said visual display presenting an image depicting kinesthetic physical movement, said visual display having at least one input electrically coupled to corresponding outputs from said at least one responsive means;

whereby said organism is trained to alter the waveform pattern of said one or more bioelectrical signals by concentrating so as to produce or change the presentation of said visual display, said visual display being presented to said organism as feedback for producing or suppressing said electrical characteristics of interest in said one or more signals, thereby achieving a desired condition of said nervous system.

30. The system of claim 29 wherein said means for detecting said bioelectrical signals comprises electrodes adapted to be coupled to said organism, means for amplifying said signals, and means for connecting between said electrodes and said amplifying means.

31. The system of claim 29 wherein at least one of said responsive means comprises a bandpass filter responsive to a preselected frequency component of said bioelectrical signal.

32. The system of claim 29 wherein at least one of said responsive means comprises means for sensing voltage amplitude responsive to an amplitude of said bioelectrical signal which is greater than a preselected minimum.

33. The system of claim 29 wherein at least one of said responsive means comprises means for sensing voltage amplitude responsive to an amplitude of said bioelectrical signal which is less than a preselected maximum.

34. The system of claim 29 wherein at least one of said responsive means comprises a bandpass filter electrically coupled to means for sensing voltage amplitude, said combination thereof being responsive to a predetermined frequency component of said bioelectrical signal having a predetermined amplitude.

35. The system of claim 29 wherein one of said bioelectrical signal detection means is disposed at one topological location in said organism's nervous system and electrically coupled to each of said plurality of responsive means.

36. The system of claim 29 wherein a plurality of bioelectrical signal detection means are disposed at a plurality of topological locations in said organism's nervous system and each is electrically coupled to a corresponding one of said plurality of responsive means.

37. The system of claim 29 wherein a plurality of bioelectrical signal detection means are disposed at a plurality of topological locations in said organism's nervous system, and wherein at least one of said detection means is electrically coupled to at least two of said plurality of responsive means, and said other detection means, if any, are each electrically coupled to one of said plurality of responsive means.

38. The system of claim 29 including therein a logic means implemented to detect when at least one of a first output signal and a plurality of first output signals is present in predetermined manner indicative of a desired condition of said organism's nervous system, said logic means providing a second output signal when said desired condition is detected, said logic means electrically coupled to said visual display, said second output signal modifying the image on said visual display.

39. The system of claim 38 including therein a timing means coupled between said logic means and said visual display, said timing means adapted to detect whether said second output signal is present for a predetermined minimum duration and, if present for a predetermined minimum duration, to pass said second output signal to modify the image on said visual display.

40. The system of claim 38 wherein said logic means detect if at least two of said plurality of first output signals are present concurrently.

41. The system of claim 38 wherein said logic means comprises means for timing intervals, said logic means providing discrete second output signal pulses to modify the visual display after a minimum time duration between subsequent second output signal pulses.

42. The system of claim 38 wherein said logic means comprises timing means for producing a discrete second output signal of desired duration 43. The system of claim 38 including means for producing an audio tone responsive to said second output signal.

44. The system of claim 38 including means for totalizing the number of times said second output signal is produced and means for presenting said total in numerical form on said visual display.

45. The system of claim 29 further comprising means for sensing if said characteristic of interest in said bioelectrical signal is present above or below a predetermined amplitude for a predetermined minimum duration, said duration sensing means coupled between said responsive means and said visual display and modifying said visual display.

46. The system of claim 29 including therein one or more means for detecting the presence of at least one undesired characteristic of interest, said detecting means providing at least one third output signal when said at least one undesired characteristic of interest is detected, said at least one detecting means coupled to said visual display, said at least one third output signal modifying the image on said visual display.

47. The system of claim 46 wherein said at least one third output signal is connected logically as a single output signal to cause a modification of the visual display.

48. The system of claim 46 wherein a plurality of detecting means causes a like plurality of distinct modifications of the visual display allowing the human organism to discern that multiple undesired characteristics of interest are present and, further, allowing the human organism to discern which of the undesired characteristics are present at any given time.

49. The system of claim 46 including means of maintaining the modified appearance of said visual display for a preselected duration once said at least one undesirable characteristic is detected.

50. The system of claim 46 including means for producing an audio tone responsive to said at least one third output signal.

51. The system of claim 46 including means for totalizing the amount of time said at least one third output signal is present and means for presenting said total in numerical form on said visual display.

52. The system of claim 46 including means for individually totalizing the amount of time each of said third output signals are present and means for presenting said individual totals in numerical form on said visual display.

53. The system of claim 29 including means for producing an audio tone responsive to the at least one first output signal.

54. The system of claim 53 including means to modulate said audio tone by the analog of said at least one first output signal.

55. The system of claim 29 wherein the audio tones produced in response to said at least one first, second and third output signals are distinct and different from one another.

56. The system of claim 29 further comprising means for:
   quantifying the amplitude of the first at least one output signal;
   totalizing the quantified amplitude of the first at least one output signal over time;
   presenting the updated, totalized and quantified amplitude of the first at least one output signal in numerical form on said visual display, or
   presenting the updated, individually totalized and quantified amplitude of the output signals in individual numerical form on said visual display;
   thereby allowing said organism to visualize the amount of said characteristics of interest being produced.

* * * * *

UNITED STATES PATENT AND TRADEMARK OFFICE
CERTIFICATE OF CORRECTION

PATENT NO. : 4,800,893
DATED : 1/31/89
INVENTOR(S) : Ross et al.

It is certified that error in the above-identified patent and that said Letters Patent is hereby corrected as shown below:

| | | |
|---|---|---|
| col. 02, line 31 | delete "typing" | insert --trying-- |
| col. 03, line 52 | delete "o" | insert --of-- |
| col. 04, line 04 | delete "lock" | insert --block-- |
| col. 04, line 15 | delete "o" | insert --of-- |
| col. 04, line 41 | after "subject" | insert --.-- |
| col. 05, line 27 | after "to" | insert --a-- |
| col. 05, line 41 | after "signal" | insert --.-- |
| col. 06, line 34 | delete "ma" | insert --may-- |
| col. 12, line 07 | after "disposed" | insert --at-- |
| col. 12, line 13 | delete "couple" | insert --coupled-- |
| col. 12, line 14 | before "one" | insert --to-- |

Signed and Sealed this

Thirteenth Day of November, 1990

*Attest:*

HARRY F. MANBECK, JR.

*Attesting Officer*     *Commissioner of Patents and Trademarks*